(12) United States Patent
Castro et al.

(10) Patent No.: US 8,647,821 B2
(45) Date of Patent: *Feb. 11, 2014

(54) METHOD AND APPARATUS FOR COMBINED ELECTROCHEMICAL SYNTHESIS AND DETECTION OF ANALYTES

(71) Applicants: Hernan A. Castro, Shingle Springs, CA (US); Gordon D. Holt, Beaverton, OR (US); Brandon C. Barnett, Beaverton, OR (US); Handong Li, San Jose, CA (US); Narayanan Sundararajan, Santa Clara, CA (US); Wei Wang, San Jose, CA (US)

(72) Inventors: Hernan A. Castro, Shingle Springs, CA (US); Gordon D. Holt, Beaverton, OR (US); Brandon C. Barnett, Beaverton, OR (US); Handong Li, San Jose, CA (US); Narayanan Sundararajan, Santa Clara, CA (US); Wei Wang, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/726,062

(22) Filed: Dec. 22, 2012

(65) Prior Publication Data

US 2013/0186767 A1    Jul. 25, 2013

Related U.S. Application Data

(60) Continuation of application No. 13/046,895, filed on Mar. 14, 2011, now Pat. No. 8,338,097, which is a division of application No. 11/646,602, filed on Dec. 28, 2006, now Pat. No. 7,923,237.

(51) Int. Cl.
| | |
|---|---|
| *C12Q 1/68* | (2006.01) |
| *C12M 1/00* | (2006.01) |
| *C12M 1/34* | (2006.01) |
| *C25B 15/02* | (2006.01) |
| *G01R 27/26* | (2006.01) |
| *H01G 4/35* | (2006.01) |
| *G01N 27/00* | (2006.01) |
| *C07H 21/00* | (2006.01) |

(52) U.S. Cl.
USPC ...... 435/6.1; 435/283.1; 435/287.2; 205/335; 205/337; 324/658; 324/679; 361/302; 422/82.01; 536/25.3; 536/25.31; 977/899

(58) Field of Classification Search
USPC ......... 435/6.1, 283.1, 287.2; 536/25.3, 25.31; 422/82.01; 361/302; 324/658, 679; 205/335, 337

See application file for complete search history.

(56) References Cited

U.S. PATENT DOCUMENTS

| | | |
|---|---|---|
| 5,143,854 A | 9/1992 | Pirrung et al. |
| 5,352,574 A | 10/1994 | Guiseppi-Elie |
| 5,405,783 A | 4/1995 | Pirrung et al. |
| 5,552,270 A | 9/1996 | Khrapko et al. |
| 5,653,930 A | 8/1997 | Noda |
| 5,653,939 A | 8/1997 | Hollis et al. |
| 5,667,667 A | 9/1997 | Southern |
| 5,766,934 A | 6/1998 | Guiseppi-Elie |
| 5,837,859 A | 11/1998 | Teoule et al. |
| 5,874,219 A | 2/1999 | Rava |
| 6,093,302 A | 7/2000 | Montgomery |
| 6,121,048 A | 9/2000 | Zaffaroni et al. |
| 6,239,273 B1 | 5/2001 | Pease et al. |
| 6,251,595 B1 | 6/2001 | Gordon et al. |
| 6,258,606 B1 | 7/2001 | Kovacs |
| 6,280,595 B1 | 8/2001 | Montgomery |
| 6,379,895 B1 | 4/2002 | Fodor et al. |
| 6,406,844 B1 | 6/2002 | Pirrung et al. |
| 6,416,952 B1 | 7/2002 | Pirrung et al. |
| 6,444,111 B1 | 9/2002 | Montgomery |
| 6,456,942 B1 | 9/2002 | Anderson |
| 6,506,558 B1 | 1/2003 | Fodor et al. |
| 6,515,039 B1 | 2/2003 | Ulbricht et al. |
| 6,518,022 B1 | 2/2003 | Sosnowski et al. |
| 6,566,495 B1 | 5/2003 | Fodor |
| 6,569,382 B1 | 5/2003 | Edman et al. |
| 6,602,400 B1 | 8/2003 | Choong et al. |
| 6,630,308 B2 | 10/2003 | Stryer et al. |
| 6,682,936 B2 | 1/2004 | Kovacs |
| 6,770,436 B1 | 8/2004 | Beecher et al. |
| 6,819,843 B1 | 11/2004 | Braun et al. |
| 6,867,048 B2 | 3/2005 | Kovacs |
| 6,919,211 B1 | 7/2005 | Fodor et al. |
| 7,622,295 B2 | 11/2009 | Cabezas |
| 7,776,269 B2 | 8/2010 | Snow et al. |
| 2004/0058438 A1 | 3/2004 | Fujii et al. |
| 2005/0014146 A1 | 1/2005 | Manaresi et al. |
| 2006/0105373 A1 | 5/2006 | Pourmand et al. |
| 2006/0263897 A1 | 11/2006 | Stapert et al. |
| 2006/0275927 A1 | 12/2006 | Dubin et al. |
| 2007/0122842 A1 | 5/2007 | Rajasekeran et al. |
| 2007/0154946 A1 | 7/2007 | Rajasekeran et al. |
| 2007/0292855 A1 | 12/2007 | Dubin et al. |
| 2008/0108149 A1 | 5/2008 | Sundararajan et al. |

(Continued)

OTHER PUBLICATIONS

Maurer K. Cooper et al., "Electrochemically generated acid and its containment to 100 micron reaction areas for the production of FNA microarrays," PloS One 1 (1): e34. doi:10.1371/journal.pone/00000034.

(Continued)

*Primary Examiner* — Dave Nguyen
*Assistant Examiner* — Narayan Bhat
(74) *Attorney, Agent, or Firm* — Pillsbury Winthrop Shaw Pittman LLP

(57) ABSTRACT

Described are devices and methods for detecting binding on an electrode surface. In addition, devices and methods for electrochemically synthesizing polymers and devices and methods for synthesizing and detecting binding to the polymer on a common integrated device surface are described.

13 Claims, 8 Drawing Sheets

(56) References Cited

U.S. PATENT DOCUMENTS

| | | |
|---|---|---|
| 2008/0161202 A1 | 7/2008 | Cabezas et al. |
| 2010/0240544 A1 | 9/2010 | Liu et al. |
| 2010/0240555 A1 | 9/2010 | Sundararajan et al. |
| 2010/0248975 A1 | 9/2010 | Tiwar et al. |

OTHER PUBLICATIONS

Egeland et al., "An electrochemical redox couple activitated by microelectrode for confined chemical patterning of surfaces," Analytical Chemistry, vol. 74, No. 7, pp. 1590-1596, Apr. 1, 2002.

Guiducci et al., "A biosensor for direct detection of DNG sequences based on capacitance measurements," Solid-state Device Research Conference, Sep. 24-26, 2002, pp. 479-482.

Pellois et al., "Individually addessable parallel peptide synthesis on microchips," Nature Biotechnology, vol. 20, Sep. 2002, pp. 922-926.

Wilson et al., "Approaches to the design of radiation-sensitive polymeric imaging systems with improved sensitivity and resolution," J. Electrochem. Soc.: Solid-State Science and Technology, vol. 133, No. 1, Jan. 1986, pp. 181-187.

Shirai et al., "Photoacid and photobase generations: chemistry and applications to polymeric materials," Prog. Polm. Sci., vol. 21, 1996, pp. 1-45.

Cameron et al., "Photogeneration of Organic Bases from o-Nitrobenzyl-Derived Carbamates," J. Am. Chem. Soc. 1991, vol. 113, pp. 4303-4313.

Cameron et al., "Base Catalysis in Imaging Materials. 1. Design and Synethsis of Novel Light-Sensitive Urethanes as Photoprecursors of Amines," J. Org. Chem. 1990, vol. 55, pp. 5919-5922.

Frechet, "The Photogeneration of Acid and Base Within Polymer Coating: Approaches to Polymer Curing and Imaging," Pure & Appl. Chem. vol. 64, No. 9, 1992, pp. 1239-1248.

Hybridization was measured by capacitance change at real time. The more repulicated targets, the bigger the capacitance change will be.

METHOD AND APPARATUS FOR COMBINED ELECTROCHEMICAL SYNTHESIS AND DETECTION OF ANALYTES

CROSS-REFERENCE TO RELATED APPLICATIONS

This application is a continuation of U.S. application Ser. No. 13/046,895 filed Mar. 14, 2011, which is a divisional to U.S. application Ser. No. 11/646,602, filed Dec. 28, 2006, which is related to U.S. application Ser. No. 11/646,600, filed Dec. 28, 2006 and U.S. application Ser. No. 11/646,615, filed Dec. 28, 2006. Each of the foregoing applications is incorporated by reference in its entirety.

FIELD OF INVENTION

The embodiments of the invention relate to devices and methods for synthesizing and detecting binding to the polymer on a common integrated device surface. The invention transcends several scientific disciplines such as polymer chemistry, biochemistry, molecular biology, medicine and medical diagnostics.

BACKGROUND

Molecular recognition (also called a binding event) is fundamental to every cellular event: transcription, translation, signal transduction, viral and bacterial infection and immune response are all mediated by selective recognition events. Thus, developing a better understanding of detecting the binding events of molecules is of significant importance.

Typical methods for carrying out on-chip analyte detections include: optical tagging (fluorescence, visible, IR, Raman), radiometric (various radioactive tag), and indirect electrochemical methods of detection (tagging with enzymes that generate charges that can be measured).

In addition, on-chip manufacturing of polymer arrays also offers the ability to create huge arrays of bio-polymers quickly and efficiently. These arrays offer huge potential in advancing the capabilities of bio-pharmaceutical drug discovery and basic academic bioresearch.

DETAILED DESCRIPTION

Figure 1:
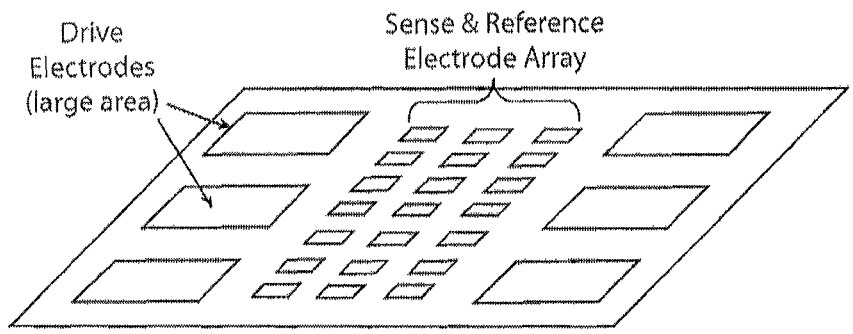
FIG. 1 is a schematic of an exposed electrode array including large area drive electrodes and micron or sub-micron scale sense and reference electrodes.

As used in the specification and claims, the singular forms "a", "an" and "the" include plural references unless the context clearly dictates otherwise. For example, the term "an array" may include a plurality of arrays unless the context clearly dictates otherwise.

An "array" is an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports. The array could either be a macroarray or a microarray, depending on the size of the sample spots on the array. A macroarray generally contains sample spot sizes of about 300 microns or larger and can be easily imaged by gel and blot scanners. A microarray would generally contain spot sizes of less than 300 microns.

"Solid support," "support," and "substrate" refer to a material or group of materials having a rigid or semi-rigid surface or surfaces. In some aspects, at least one surface of the solid support will be substantially flat, although in some aspects it may be desirable to physically separate synthesis regions for different molecules with, for example, wells, raised regions, pins, etched trenches, or the like. In certain aspects, the solid support(s) will take the form of beads, resins, gels, microspheres, or other geometric configurations.

The term "probe" or "probe molecule" refers to a molecule attached to the substrate of the array, which is typically cDNA or pre-synthesized polynucleotide deposited on the array. Probes molecules are biomolecules capable of undergoing binding or molecular recognition events with target molecules. (In some references, the terms "target" and "probe" are defined opposite to the definitions provided here.) The polynucleotide probes require only the sequence information of genes, and thereby can exploit the genome sequences of an organism. In cDNA arrays, there could be cross-hybridization due to sequence homologies among members of a gene family. Polynucleotide arrays can be specifically designed to differentiate between highly homologous members of a gene family as well as spliced forms of the same gene (exon-specific). Polynucleotide arrays of the embodiment of this invention could also be designed to allow detection of mutations and single nucleotide polymorphism.

The term "target" or "target molecule" refers to a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to molecular probes such as chemically modified carbon nanotubes, carbon nanotube bundles, nanowires and nanoparticles. The target molecule may be fluorescently labeled DNA or RNA.

The terms "die," "polymer array chip," "DNA array," "array chip," "DNA array chip," "bio-chip" or "chip" are used interchangeably and refer to a collection of a large number of probes arranged on a shared substrate which could be a portion of a silicon wafer, a nylon strip or a glass slide.

The term "molecule" generally refers to a macromolecule or polymer as described herein. However, arrays comprising single molecules, as opposed to macromolecules or polymers, are also within the scope of the embodiments of the invention.

"Predefined region" or "spot" or "pad" refers to a localized area on a solid support which is, was, or is intended to be used for formation of a selected molecule and is otherwise referred to herein in the alternative as a "selected" region. The predefined region may have any convenient shape, e.g., circular, rectangular, elliptical, wedge-shaped, etc. For the sake of brevity herein, "predefined regions" are sometimes referred to simply as "regions" or "spots." In some embodiments, a predefined region and, therefore, the area upon which each distinct molecule is synthesized is smaller than about 1 $cm^2$ or less than 1 $mm^2$, and still more preferably less than 0.5 $mm^2$. In most preferred embodiments the regions have an area less than about 10,000 $\mu m^2$ or, more preferably, less than 100 $\mu m^2$. Additionally, multiple copies of the polymer will typically be synthesized within any preselected region. The number of copies can be in the thousands to the millions. More preferably, a die of a wafer contains at least 400 spots in, for example, an at least 20×20 matrix. Even more preferably, the die contains at least 2048 spots in, for example, an at least 64×32 matrix, and still more preferably, the die contains at least 204,800 spots in, for example, an at least 640×320 array. A spot could contain an electrode to generate an electrochemical reagent, a working electrode to synthesize a polymer and a confinement electrode to confine the generated electrochemical reagent. The electrode to generate the electrochemical reagent could be of any shape, including, for example, circular, flat disk shaped and hemisphere shaped.

An "electrode" is a body or a location at which an electrochemical reaction occurs. The term "electrochemical" refers to an interaction or interconversion of electric and chemical phenomena.

A "functionalized electrode" is an electrode of a microchip array having a probe molecule that has a specific chemical affinity to a target molecule. An "unfunctionalized electrode" is an electrode of a microchip array having no probe molecule or having a probe molecule that has no specific chemical affinity to a target molecule.

The electrodes used in embodiments of the invention may be composed of, but are not limited to, metals such as iridium and/or platinum, and other metals, such as, palladium, gold, silver, copper, mercury, nickel, zinc, titanium, tungsten, aluminum, as well as alloys of various metals, and other conducting materials, such as, carbon, including glassy carbon, reticulated vitreous carbon; basal plane graphite, edge plane graphite and graphite. Doped oxides such as indium tin oxide, and semiconductors such as silicon oxide and gallium arsenide are also contemplated. Additionally, the electrodes may be composed of conducting polymers, metal doped polymers, conducting ceramics and conducting clays. Among the metals, platinum and palladium are especially preferred because of the advantageous properties associated with their ability to absorb hydrogen, i.e., their ability to be "preloaded" with hydrogen before being used in the methods of the invention.

The electrodes may be connected to an electric source in any known manner. Preferred ways of connecting the electrodes to the electric source include CMOS (complementary metal oxide semiconductor) switching circuitry, radio and microwave frequency addressable switches, light addressable switches, direct connection from an electrode to a bond pad on the perimeter of a semiconductor chip, and combinations thereof. CMOS switching circuitry involves the connection of each of the electrodes to a CMOS transistor switch. The switch could be accessed by sending an electronic address signal down a common bus to SRAM (static random access memory) circuitry associated with each electrode. When the switch is "on", the electrode is connected to an electric source. Radio and microwave frequency addressable switches involve the electrodes being switched by a RF or microwave signal. This allows the switches to be thrown both with and/or without using switching logic. The switches can be tuned to receive a particular frequency or modulation frequency and switch without switching logic. Light addressable switches are switched by light. In this method, the electrodes can also be switched with and without switching logic. The light signal can be spatially localized to afford switching without switching logic. This could be accomplished, for example, by scanning a laser beam over the electrode array; the electrode being switched each time the laser illuminates it.

In some aspects, a predefined region can be achieved by physically separating the regions (i.e., beads, resins, gels, etc.) into wells, trays, etc.

A "protecting group" is a moiety which is bound to a molecule and designed to block one reactive site in a molecule, but may be spatially removed upon selective exposure to an activator or a deprotecting reagent. Several examples of protecting groups are known in the literature. The proper selection of protecting group (also known as protective group) for a particular synthesis would be governed by the overall methods employed in the synthesis. Activators include, for example, electromagnetic radiation, ion beams, electric fields, magnetic fields, electron beams, x-ray, and the like. A deprotecting reagent could include, for example, an acid, a base or a free radical. Protective groups are materials that bind to a monomer, a linker molecule or a pre-formed molecule to protect a reactive functionality on the monomer, linker molecule or pre-formed molecule, which may be removed upon selective exposure to an activator, such as an electrochemically generated reagent. Protective groups that may be used in accordance with an embodiment of the invention preferably include all acid and base labile protecting groups. For example, peptide amine groups are preferably protected by t-butyloxycarbonyl (BOC) or benzyloxycarbonyl (CBZ), both of which are acid labile, or by 9-fluorenylmethoxycarbonyl (FMOC), which is base labile. Additionally, hydroxyl groups on phosphoramidites may be protected by dimethoxytrityl (DMT), which is acid labile. Exocyclic amine groups on nucleosides, in particular on phosphoramidites, are preferably protected by dimethylformamidine on the adenosine and guanosine bases, and isobutyryl on the cytidine bases, both of which are base labile protecting groups. This protection strategy is known as fast oligonucleotide deprotection (FOD).

Any unreacted deprotected chemical functional groups may be capped at any point during a synthesis reaction to avoid or to prevent further bonding at such molecule. Capping groups "cap" deprotected functional groups by, for example, binding with the unreacted amino functions to form amides. Capping agents suitable for use in an embodiment of the invention include: acetic anhydride, n-acetylimidizole, isopropenyl formate, fluorescamine, 3-nitrophthalic anhydride and 3-sulfoproponic anhydride. Of these, acetic anhydride and n-acetylimidizole are preferred.

Additional protecting groups that may be used in accordance with an embodiment of the invention include acid labile groups for protecting amino moieties: tertbutyloxycarbonyl,-tert-amyloxycarbonyl, adamantyloxycarbonyl, 1-methylcyclobutyloxycarbonyl, 2-(p-biphenyl)propyl(2)oxycarbonyl, 2-(p-phenylazophenylyl)propyl(2)oxycarbonyl, .alpha.,.alpha.-dimethyl-3,5-dimethyloxybenzyloxy-carbonyl, 2-phenylpropyl(2)oxycarbonyl, 4-methyloxybenzyloxycarbonyl, benzyloxycarbonyl, furfuryloxycarbonyl, triphenylmethyl (trityl), p-toluenesulfenylaminocarbonyl, dimethylphosphinothioyl, diphenylphosphinothioyl, 2-benzoyl-1-methylvinyl, o-nitrophenylsulfenyl, and 1-naphthylidene; as base labile groups for protecting amino moieties: 9-fluorenylmethyloxycarbonyl, methylsulfonylethyloxycarbonyl, and 5-benzisoazolylmethyleneoxycarbonyl; as groups for protecting amino moieties that are labile when reduced: dithiasuccinoyl, p-toluene sulfonyl, and piperidino-oxycarbonyl; as groups for protecting amino moieties that are labile when oxidized: (ethylthio)carbonyl; as groups for protecting amino moieties that are labile to miscellaneous reagents, the appropriate agent is listed in parenthesis after the group: phthaloyl (hydrazine), trifluoroacetyl (piperidine), and chloroacetyl (2-aminothiophenol); acid labile groups for protecting carboxylic acids: tert-butyl ester; acid labile groups for protecting hydroxyl groups: dimethyltrityl; and basic labile groups for protecting phosphotriester groups: cyanoethyl.

An "electrochemical reagent" refers to a chemical generated at a selected electrode by applying a sufficient electrical potential to the selected electrode and is capable of electrochemically removing a protecting group from a chemical functional group. The chemical group would generally be attached to a molecule. Removal of a protecting group, or "deprotection," in accordance with the invention, preferably occurs at a particular portion of a molecule when a chemical reagent generated by the electrode acts to deprotect or remove, for example, an acid or base labile protecting group from the molecule. This electrochemical deprotection reaction may be direct, or may involve one or more intermediate chemical reactions that are ultimately driven or controlled by the imposition of sufficient electrical potential at a selected electrode.

Electrochemical reagents that can be generated electrochemically at an electrode fall into two broad classes: oxidants and reductants. Oxidants that can be generated electrochemically, for example, include iodine, iodate, periodic acid, hydrogen peroxide, hypochlorite, metavanadate, bromate, dichromate, cerium (IV), and permanganate ions. Reductants that can be generated electrochemically, for example, include chromium (II), ferrocyanide, thiols, thiosulfate, titanium (III), arsenic (III) and iron (II) ions. The miscellaneous reagents include bromine, chloride, protons and hydroxyl ions. Among the foregoing reagents, protons, hydroxyl, iodine, bromine, chlorine and thiol ions are preferred.

The generation of and electrochemical reagent of a desired type of chemical species requires that the electric potential of the electrode that generates the electrochemical reagent have a certain value, which may be achieved by specifying either the voltage or the current. There are two ways to achieve the desired potential at this electrode: either the voltage may be specified at a desired value or the current can be determined such that it is sufficient to provide the desired voltage. The range between the minimum and maximum potential values could be determined by the type of electrochemical reagent chosen to be generated.

An "activating group" refers to those groups which, when attached to a particular chemical functional group or reactive site, render that site more reactive toward covalent bond formation with a second chemical functional group or reactive site.

A "polymeric brush" ordinarily refers to polymer films comprising chains of polymers that are attached to the surface of a substrate. The polymeric brush could be a functionalized polymer films which comprise functional groups such as hydroxyl, amino, carboxyl, thiol, amide, cyanate, thiocyanate, isocyanate and isothio cyanate groups, or a combination thereof, on the polymer chains at one or more predefined regions. The polymeric brushes of the embodiment of the invention are capable of attachment or stepwise synthesis of macromolecules thereon.

A "linker" molecule refers to any of those molecules described supra and preferably should be about 4 to about 40 atoms long to provide sufficient exposure. The linker molecules may be, for example, aryl acetylene, ethylene glycol oligomers containing 2-10 monomer units, diamines, diacids, amino acids, among others, and combinations thereof. Alternatively, the linkers may be the same molecule type as that being synthesized (i.e., nascent polymers), such as polynucleotides, oligopeptides, or oligosaccharides.

The linker molecule or substrate itself and monomers used herein are provided with a functional group to which is bound a protective group. Generally, the protective group is on the distal or terminal end of a molecule. Preferably, the protective group is on the distal or terminal end of the linker molecule opposite the substrate. The protective group may be either a negative protective group (i.e., the protective group renders the linker molecules less reactive with a monomer upon exposure) or a positive protective group (i.e., the protective group renders the linker molecules more reactive with a monomer upon exposure). In the case of negative protective groups, there could be an additional step of reactivation. In some embodiments, this will be done by heating.

The polymer brush or the linker molecule may be provided with a cleavable group at an intermediate position, which group can be cleaved with an electrochemically generated reagent. This group is preferably cleaved with a reagent different from the reagent(s) used to remove the protective groups. This enables removal of the various synthesized polymers or nucleic acid sequences following completion of the synthesis. The cleavable group could be acetic anhydride, n-acetylimidizole, isopropenyl formate, fluorescamine, 3-nitrophthalic anhydride and 3-sulfoproponic anhydride. Of these, acetic anhydride and n-acetylimidizole are preferred.

The polymer brush or the linker molecule could be of sufficient length to permit polymers on a completed substrate to interact freely with binding entities (monomers, for example) exposed to the substrate. The polymer brush or the linker molecule, when used, could preferably be long enough to provide sufficient exposure of the functional groups to the binding entity. The linker molecules may include, for example, aryl acetylene, ethylene glycol oligomers containing from 2 to 20 monomer units, diamines, diacids, amino acids, and combinations thereof. Other linker molecules may be used in accordance with the different embodiments of the present invention and will be recognized by those skilled in the art in light of this disclosure. In one embodiment, derivatives of the acid labile 4,4'-dimethyoxytrityl molecules with an exocyclic active ester can be used in accordance with an embodiment of the invention. More preferably, N-succinimidyl-4[bis-(4-methoxyphenyl)-chloromethyl]-benzoate is used as a cleavable linker molecule during DNA synthesis. Alternatively, other manners of cleaving can be used over the entire array at the same time, such as chemical reagents, light or heat.

A "free radical initiator" or "initiator" is a compound that can provide a free radical under certain conditions such as heat, light, or other electromagnetic radiation, which free radical can be transferred from one monomer to another and thus propagate a chain of reactions through which a polymer may be formed. Several free radical initiators are known in the art, such as azo, nitroxide, and peroxide types, or those comprising multi-component systems.

"Living free radical polymerization" is defined as a living polymerization process wherein chain initiation and chain propagation occur without significant chain termination reactions. Each initiator molecule produces a growing monomer chain which continuously propagates until all the available monomer has been reacted. Living free radical polymerization differs from conventional free radical polymerization where chain initiation, chain propagation and chain termination reactions occur simultaneously and polymerization continues until the initiator is consumed. Living free radical polymerization facilitates control of molecular weight and molecular weight distribution. Living free radical polymerization techniques, for example, involve reversible end capping of growing chains during polymerization. One example is atom transfer radical polymerization (ATRP).

A "radical generation site" is a site on an initiator wherein free radicals are produced in response to heat or electromagnetic radiation.

A "polymerization terminator" is a compound that prevents a polymer chain from further polymerization. These compounds may also be known as "terminators," or "capping agents" or "inhibitors." Various polymerization terminators are known in the art. In one aspect, a monomer that has no free hydroxyl groups may act as a polymerization terminator.

The term "capable of supporting polymer array synthesis" refers to any body on which polymer array synthesis can be carried out, e.g., a polymeric brush that is functionalized with functional groups such as hydroxyl, amino, carboxyl etc. These functional groups permit macromolecular synthesis by acting as "attachment points."

The monomers in a given polymer or macromolecule can be identical to or different from each other. A monomer can be a small or a large molecule, regardless of molecular weight. Furthermore, each of the monomers may be protected members which are modified after synthesis.

"Monomer" as used herein refers to those monomers that are used to a form a polymer. However, the meaning of the monomer will be clear from the context in which it is used. The monomers for forming the polymers of the embodiments of the invention, e.g., a polymeric brush or a linker molecule, have for example the general structure:

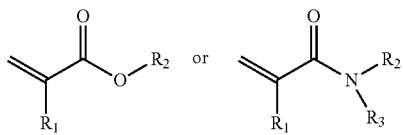

wherein $R_1$ is hydrogen or lower alkyl; $R_2$ and $R_3$ are independently hydrogen, or —Y—Z, wherein Y is lower alkyl, and Z is hydroxyl, amino, or C(O)—R, where R is hydrogen, lower alkoxy or aryloxy.

The term "alkyl" refers to those groups such as methyl, ethyl, propyl, butyl etc, which may be linear, branched or cyclic.

The term "alkoxy" refers to groups such as methoxy, ethoxy, propoxy, butoxy, etc., which may be linear, branched or cyclic.

The term "lower" as used in the context of lower alkyl or lower alkoxy refers to groups having one to six carbons.

The term "aryl" refers to an aromatic hydrocarbon ring to which is attached an alkyl group. The term "aryloxy" refers to an aromatic hydrocarbon ring to which is attached an alkoxy group. One of ordinary skill in the art would readily understand these terms.

Other monomers for preparing macromolecules of the embodiments of the invention are well-known in the art. For example, when the macromolecule is a peptide, the monomers include, but are not restricted to, for example, amino acids such as the L-amino acids, the D-amino acids, the synthetic and/or natural amino acids. When the macromolecule is a nucleic acid, or polynucleotide, the monomers include any nucleotide. When the macromolecule is a polysaccharide, the monomers can be any pentose, hexose, heptose, or their derivatives.

A "monomer addition cycle" is a cycle comprising the chemical reactions necessary to produce covalent attachment of a monomer to a nascent polymer or linker, such as to elongate the polymer with the desired chemical bond (e.g., 5'-3' phosphodiester bond, peptide bond, etc.). For example, and not to limit the invention, the following steps typically comprise a monomer addition cycle in phosphoramidite-based polynucleotide synthesis: (1) deprotection, comprising removal of the DMT group from a 5'-protected nucleoside (which may be part of a nascent polynucleotide) wherein the 5'-hydroxyl is blocked by covalent attachment of DMT, such deprotection is usually done with a suitable deprotection reagent (e.g., a protic acid: trichloroacetic acid or dichloroacetic acid), and may include physical removal (e.g., washing, such as with acetonitrile) of the removed protecting group (e.g., the cleaved dimethyltrityl group), (2) coupling, comprising reacting a phosphoramidite nucleoside(s), often activated with tetrazole, with the deprotected nucleoside, (3) optionally including capping, to truncate unreacted nucleosides from further participation in subsequent monomer addition cycles, such as by reaction with acetic anhydride and N-methylimidazole to acetylate free 5'-hydroxyl groups, and (4) oxidation, such as by iodine in tetrahydrofuran/water/pyridine, to convert the trivalent phosphite triester linkage to a pentavalent phosphite triester, which in turn can be converted to a phosphodiester via reaction with ammonium hydroxide. Thus, with respect to phosphoramidite synthesis of polynucleotides, the following reagents are typically necessary for a complete monomer addition cycle: trichloroacetic acid or dichloroacetic acid, a phosphoramidite nucleoside, an oxidizing agent, such as iodine (e.g., iodine/water/THF/pyridine), and optionally N-methylimidazole for capping.

A "macromolecule" or "polymer" comprises two or more monomers covalently joined. The monomers may be joined one at a time or in strings of multiple monomers, ordinarily known as "oligomers." Thus, for example, one monomer and a string of five monomers may be joined to form a macromolecule or polymer of six monomers. Similarly, a string of fifty monomers may be joined with a string of hundred monomers to form a macromolecule or polymer of one hundred and fifty monomers. The term polymer as used herein includes, for example, both linear and cyclic polymers of nucleic acids, polynucleotides, polynucleotides, polysaccharides, oligosaccharides, proteins, polypeptides, peptides, phospholipids and peptide nucleic acids (PNAs). The peptides include those peptides having either α-, β-, or ω-amino acids. In addition, polymers include heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent upon review of this disclosure.

A "nanomaterial" as used herein refers to a structure, a device or a system having a dimension at the atomic, molecular or macromolecular levels, in the length scale of approximately 1-100 nanometer range. Preferably, a nanomaterial has properties and functions because of the size and can be manipulated and controlled on the atomic level.

A "carbon nanotube" refers to a fullerene molecule having a cylindrical or toroidal shape. A "fullerene" refers to a form of carbon having a large molecule consisting of an empty cage of sixty or more carbon atoms.

The term "nucleotide" includes deoxynucleotides and analogs thereof. These analogs are those molecules having some structural features in common with a naturally occurring nucleotide such that when incorporated into a polynucleotide sequence, they allow hybridization with a complementary polynucleotide in solution. Typically, these analogs are derived from naturally occurring nucleotides by replacing and/or modifying the base, the ribose or the phosphodiester moiety. The changes can be tailor-made to stabilize or destabilize hybrid formation, or to enhance the specificity of hybridization with a complementary polynucleotide sequence as desired, or to enhance stability of the polynucleotide.

The term "polynucleotide" or "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. Polynucleotides of the embodiments of the invention include sequences of deoxyribopolynucleotide (DNA), ribopolynucleotide (RNA), or DNA copies of ribopolynucleotide (cDNA) which may be isolated from natural sources, recombinantly produced, or artificially synthesized. A further example of a polynucleotide of the embodiments of the invention may be polyamide polynucleotide (PNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The polymers made of nucleotides such as nucleic acids, polynucleotides and polynucleotides may also be referred to herein as "nucleotide polymers.

An "oligonucleotide" is a polynucleotide having 2 to 20 nucleotides. Phosphoramidites protected in this manner are known as FOD phosphoramidites.

Analogs also include protected and/or modified monomers as are conventionally used in polynucleotide synthesis. As one of skill in the art is well aware, polynucleotide synthesis uses a variety of base-protected nucleoside derivatives in which one or more of the nitrogens of the purine and pyrimidine moiety are protected by groups such as dimethoxytrityl, benzyl, tert-butyl, isobutyl and the like.

For instance, structural groups are optionally added to the ribose or base of a nucleoside for incorporation into a polynucleotide, such as a methyl, propyl or allyl group at the 2'-O position on the ribose, or a fluoro group which substitutes for the 2'-O group, or a bromo group on the ribonucleoside base. 2'-O-methyloligoribonucleotides (2'-O-MeORNs) have a higher affinity for complementary polynucleotides (especially RNA) than their unmodified counterparts. Alternatively, deazapurines and deazapyrimidines in which one or more N atoms of the purine or pyrimidine heterocyclic ring are replaced by C atoms can also be used.

The phosphodiester linkage, or "sugar-phosphate backbone" of the polynucleotide can also be substituted or modified, for instance with methyl phosphonates, O-methyl phosphates or phosphororthioates. Another example of a polynucleotide comprising such modified linkages for purposes of this disclosure includes "peptide polynucleotides" in which a polyamide backbone is attached to polynucleotide bases, or modified polynucleotide bases. Peptide polynucleotides which comprise a polyamide backbone and the bases found in naturally occurring nucleotides are commercially available.

Nucleotides with modified bases can also be used in the embodiments of the invention. Some examples of base modifications include 2-aminoadenine, 5-methylcytosine, 5-(propyn-1-yl)cytosine, 5-(propyn-1-yl)uracil, 5-bromouracil, 5-bromocytosine, hydroxymethylcytosine, methyluracil, hydroxymethyluracil, and dihydroxypentyluracil which can be incorporated into polynucleotides in order to modify binding affinity for complementary polynucleotides.

Groups can also be linked to various positions on the nucleoside sugar ring or on the purine or pyrimidine rings which may stabilize the duplex by electrostatic interactions with the negatively charged phosphate backbone, or through interactions in the major and minor groves. For example, adenosine and guanosine nucleotides can be substituted at the $N^2$ position with an imidazolyl propyl group, increasing duplex stability. Universal base analogues such as 3-nitropyrrole and 5-nitroindole can also be included. A variety of modified polynucleotides suitable for use in the embodiments of the invention are described in the literature.

When the macromolecule of interest is a peptide, the amino acids can be any amino acids, including α, β, or ω-amino acids. When the amino acids are α-amino acids, either the L-optical isomer or the D-optical isomer may be used. Additionally, unnatural amino acids, for example, β-alanine, phenylglycine and homoarginine are also contemplated by the embodiments of the invention. These amino acids are well-known in the art.

A "peptide" is a polymer in which the monomers are amino acids and which are joined together through amide bonds and alternatively referred to as a polypeptide. In the context of this specification it should be appreciated that the amino acids may be the L-optical isomer or the D-optical isomer. Peptides are two or more amino acid monomers long, and often more than 20 amino acid monomers long.

A "protein" is a long polymer of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are essential for the structure, function, and regulation of the body's cells, tissues, and organs, and each protein has unique functions. Examples are hormones, enzymes, and antibodies.

The term "sequence" refers to the particular ordering of monomers within a macromolecule and it may be referred to herein as the sequence of the macromolecule.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." For example, hybridization refers to the formation of hybrids between a probe polynucleotide (e.g., a polynucleotide of the invention which may include substitutions, deletion, and/or additions) and a specific target polynucleotide (e.g., an analyte polynucleotide) wherein the probe preferentially hybridizes to the specific target polynucleotide and substantially does not hybridize to polynucleotides consisting of sequences which are not substantially complementary to the target polynucleotide, However, it will be recognized by those of skill that the minimum length of a polynucleotide desired for specific hybridization to a target polynucleotide will depend on several factors: G/C content, positioning of mismatched bases (if any), degree of uniqueness of the sequence as compared to the population of target polynucleotides, and chemical nature of the polynucleotide (e.g., methylphosphonate backbone, phosphorothiolate, etc.), among others.

Methods for conducting polynucleotide hybridization assays have been well developed in the art. Hybridization assay procedures and conditions will vary depending on the application and are selected in accordance with the general binding methods known in the art.

It is appreciated that the ability of two single stranded polynucleotides to hybridize will depend upon factors such as their degree of complementarity as well as the stringency of the hybridization reaction conditions.

As used herein, "stringency" refers to the conditions of a hybridization reaction that influence the degree to which polynucleotides hybridize. Stringent conditions can be selected that allow polynucleotide duplexes to be distinguished based on their degree of mismatch. High stringency is correlated with a lower probability for the formation of a duplex containing mismatched bases. Thus, the higher the stringency, the greater the probability that two single-stranded polynucleotides, capable of forming a mismatched duplex, will remain single-stranded. Conversely, at lower stringency, the probability of formation of a mismatched duplex is increased.

The appropriate stringency that will allow selection of a perfectly-matched duplex, compared to a duplex containing one or more mismatches (or that will allow selection of a particular mismatched duplex compared to a duplex with a higher degree of mismatch) is generally determined empirically. Means for adjusting the stringency of a hybridization reaction are well-known to those of skill in the art.

A "ligand" is a molecule that is recognized by a particular receptor. Examples of ligands that can be investigated by this invention include, but are not restricted to, agonists and antagonists for cell membrane receptors, toxins and venoms, viral epitopes, hormones, hormone receptors, peptides, enzymes, enzyme substrates, cofactors, drugs (e.g. opiates, steroids, etc.), lectins, sugars, polynucleotides, nucleic acids, oligosaccharides, proteins, and monoclonal antibodies.

A "receptor" is molecule that has an affinity for a given ligand. Receptors may-be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended, A "Ligand Receptor Pair" is formed when two macromolecules have combined through molecular recognition to form a complex. Other examples of receptors which can be investigated by this invention include but are not restricted to:

a) Microorganism receptors: Determination of ligands which bind to receptors, such as specific transport proteins or enzymes essential to survival of microorganisms, is useful in developing a new class of antibiotics. Of particular value would be antibiotics against opportunistic fungi, protozoa, and those bacteria resistant to the antibiotics in current use.

b) Enzymes: For instance, one type of receptor is the binding site of enzymes such as the enzymes responsible for cleaving neurotransmitters; determination of ligands which bind to certain receptors to modulate the action of the enzymes which cleave the different neurotransmitters is useful in the development of drugs which can be used in the treatment of disorders of neurotransmission.

c) Antibodies: For instance, the invention may be useful in investigating the ligand-binding site on the antibody molecule which combines with the epitope of an antigen of interest; determining a sequence that mimics an antigenic epitope may lead to the-development of vaccines of which the immunogen is based on one or more of such sequences or lead to the development of related diagnostic agents or compounds useful in therapeutic treatments such as for auto-immune diseases (e.g., by blocking the binding of the "anti-self" antibodies).

d) Nucleic Acids: Sequences of nucleic acids may be synthesized to establish DNA or RNA binding sequences.

e) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant.

f) Hormone receptors: Examples of hormones receptors include, e.g., the receptors for insulin and growth hormone. Determination of the ligands which bind with high affinity to a receptor is useful in the development of, for example, an oral replacement of the daily injections which diabetics take to relieve the symptoms of diabetes. Other examples are the vasoconstrictive hormone receptors; determination of those ligands which bind to a receptor may lead to the development of drugs to control blood pressure.

g) Opiate receptors: Determination of ligands which bind to the opiate receptors in the brain is useful in the development of less-addictive replacements for morphine and related drugs.

The term "complementary" refers to the topological compatibility or matching together of interacting surfaces of a ligand molecule and its receptor. Thus, the receptor and its ligand can be described as complementary, and furthermore, the contact surface characteristics are complementary to each other.

A "scribe line" is typically an "inactive" area between the active dies that provide area for separating the die (usually with a saw). Often, metrology and alignment features populate this area.

A "via" refers to a hole etched in the interlayer of a dielectric which is then filled with an electrically conductive material, preferably tungsten, to provide vertical electrical connection between stacked up interconnect metal lines that are capable of conducting electricity.

"Metal lines" within a die are interconnect lines. Metal interconnect lines do not typically cross the scribe line boundary to electrically connect two dies or, as in the some embodiments of this invention, a multitude of die to one or more wafer pads.

The term "oxidation" means losing electron to oxidize. The term "reduction" means gaining electrons to reduce. The term "redox reaction" refers to any chemical reaction which involves oxidation and reduction.

The term "wafer" means a semiconductor substrate. A wafer could be fashioned into various sizes and shapes. It could be used as a substrate for a microchip. The substrate could be overlaid or embedded with circuitry, for example, a pad, via, an interconnect or a scribe line. The circuitry of the wafer could also serve several purpose, for example, as microprocessors, memory storage, and/or communication capabilities. The circuitry can be controlled by the microprocessor on the wafer itself or controlled by a device external to the wafer.

The term "molecular binding event" means the occurrence of contact between a probe molecule and a target molecule. The devices for detecting a molecular binding event according to the embodiments of the present invention are intended for use in a molecular recognition-based assay for the analysis of a sample suspected of containing one or more target molecules or moieties such as specific nucleic acid sequences. The probe molecules of the array are provided for the purpose of binding and detecting specific target molecules, e.g., nucleic acid sequences. The hybridization between the probe and target nucleic acid sequences may occur through the standard Watson-Crick hydrogen-bonding interactions or other known specific binding interactions known in the art.

The term "polarization change" means a change in the amount of charge on an electrode produced by the deposition of a target molecule.

The term "differential amplifier" means a device that amplifies the difference between two input signals (−) and (+). This amplifier is also referred to as a differential-input single-ended output amplifier. It is a precision voltage difference amplifier, and could form the central basis of more sophisticated instrumentation amplifier circuits.

The term "field effect transistor" (FET) is a family of transistors that rely on an electric field to control the conductivity of a "channel" in a semiconductor material, FETs, like all transistors, can be thought of as voltage-controlled resistors. Most FETs are made using conventional bulk semiconductor processing techniques, using the single-crystal semiconductor wafer as the active region, or channel.

The term "CMOS" means complementary metal oxide semiconductor.

One embodiment of a method for detecting the binding of an analyte to an electrode surface includes exposing an electrode to one or more analytes, and detecting a change in charge or effective capacitance on a surface of the electrode utilizing an integrating charge amplifier.

Preferably, the binding is DNA hybridization, peptide/protein binding, peptide phosphorylation, or aptamer/protein binding. Preferably, the analyte is in a conductive solution. Preferred solutions include aqueous solutions and conductive gels.

Preferably, the method further includes applying a pulse to a solution comprising the analyte to accumulate a charge over a fixed time. Preferably, the method also further includes applying a calibrating reference voltage pulse to an internal test capacitor to normalize the response of the integrating charge amplifier.

Preferably, the charge is converted to a voltage through a two stage integrating charge amplifier. Preferably, the electrode is part of an array of electrodes fabricated on a single substrate. Preferably, a reference electrode is utilized to provide differential measurements of change in charge and effective capacitance. The electrode may be provided on a chip comprising a 1 bit latch configured to store a response of the amplifier to a drive or reference pulse.

An embodiment of a device configured to detect the binding of an analyte to an electrode surface includes a substrate, an electrode on the surface of the substrate, and an integrating charge amplifier connected to the electrode and configured to detect a change in charge or effective capacitance on a surface of the electrode.

An embodiment of a method for synthesizing a polymer on a chip includes providing a chip including an electrode connected to both drive circuitry and an integrating charge amplifier, exposing the electrode to one or more polymer bases, and providing a voltage to the surface of the electrode to bind the one or more polymer basis on the electrode surface.

Preferably, the polymer is a DNA oligonucleotide, a peptide, or an aptamer. Preferably, latches are provided to allow the electrode to exist in three states driven by voltage 1, driven by voltage 2, or floated during a synthesis cycle. Preferably, the voltage creates an acidic or basic field that deprotects a polymer base so that it binds on electrode surface. Preferably, the polymer bases are in an aqueous solution or conductive gel. Preferably, the electrode is part of an array of electrodes fabricated on a single substrate.

An embodiment of a device configured to synthesize a polymer includes a substrate, an electrode on the surface of the substrate, and an integrating charge amplifier connected to the electrode and configured to apply a voltage to the surface of the electrode.

An embodiment of a device configured for combined synthesis and detection of analytes includes a substrate, an electrode on the surface of the substrate, and circuitry connected to the electrode and configured to apply a voltage to the surface of the electrode to drive polymer synthesis and connect the same electrodes to integrating charge amplifiers.

Preferably, the analyte is a DNA oligonucleotide, a peptide, or an aptamer. Preferably, the device further includes two latches configured to allow the electrode to exist in three states driven by voltage 1, driven by voltage 2, or floated during a synthesis cycle.

Preferably, the voltage creates an acidic or basic field that deprotects a polymer base so that it binds on electrode surface. Preferably, the polymer bases are in an aqueous solution or conductive gel. Preferably, the device includes an array of electrodes fabricated on a single substrate.

Described are methods for real-time detection of the binding of analytes. The devices do not require tagging, such as fluorescent tagging, in order to detect analytes. The methods are also potentially more sensitive than many methods of detection, which may reduce the need for amplification if DNA is being detected. For example, experiments show charge detection with ~5 fF resolution. The devices and method also potentially offer a much broader dynamic range of operation, potentially as much as 7 orders of magnitude by precise control of manufacturing and layout parameters (e.g. effective electrode area, amplifier gain, affinity probe uniformity, etc).

The same devices can also be used to synthesis polymers, particularly bio-polymers. The devices and methods offer unprecedented capabilities for highly flexible polymer microarray synthesis at micron and sub-micron scale with reproducibility driven by CMOS manufacturing.

One embodiment is a method and apparatus for real-time detection of the binding of analytes. More specifically, the methods and apparatuses detect binding on an electrode surface or to an affinity probe attached to an electrode surface on a CMOS device. The device may be made in a standard or modified CMOS process flow by one skilled in the art.

The device can be used to detect a wide variety of analyte bindings to the electrode surface in many cases by attachment of an appropriate affinity probe. Preferred bindings include, but are not limited to, DNA hybridization, peptide/protein binding, peptide phosphorylation, aptamer/protein binding and chemical bindings and adsorption.

Preferred detection devices include those that can be monolithically integrated with the synthesis devices, for example field effect devices (direct and floating gate), impedance spectroscopy devices, integrating charge amplifiers, and optical devices capable of being integrated with electrochemical synthesis devices. More preferred devices include integrating charge amplifiers.

One preferred embodiment of the integrating charge amplifier design includes several components that can be implemented by one skilled in the art in a traditional or modified CMOS process/fabrication process. The first element is a drive circuit that provides voltage pulses (can be a variety of waveforms: square, sine, saw tooth, etc) to an exposed drive electrode (i.e. accessible to the introduction of analyte, fluid, or gas). The second is an integrating charge amplifier that has one input as an exposed sensing electrode and the other as an exposed or unexposed reference electrode.

The exposed reference electrode allows for common mode noise rejection by inputting to one input of the amplifier a signal representing the same environmental conditions (pH, temperature, ion concentration, non-binding analytes, etc). Alternatively, the reference capacitor can be exposed to air or covered to establish an absolute reference. An example, of such an embodiment is described below with respect to FIG. 5.

To the sense electrodes, affinity probes can be attached through chemical methods. The reference electrode may or may not have a similar or different affinity probe attached and each sensing electrode can have a different affinity probe attached to detect a variety of analytes (e.g. multiple genes in a sample). The integrated charge value can be converted to a voltage through a two stage amplifier. An internal (not exposed, monolithic NMOS or Metal-Insulator-Metal) capacitor may be connected to the amplifier via an internal switch to be used as a reference capacitor. These elements provide the driving, sensing, and referencing capability of the device. FIG. 1 shows these elements in each reference configuration. In FIG. 1 shows an exposed electrode array including large area drive electrodes and micron or sub-micron scale sense and reference electrodes. The array can be of any density manufacturable by standard semiconductor fabrication techniques.

Figure 2:
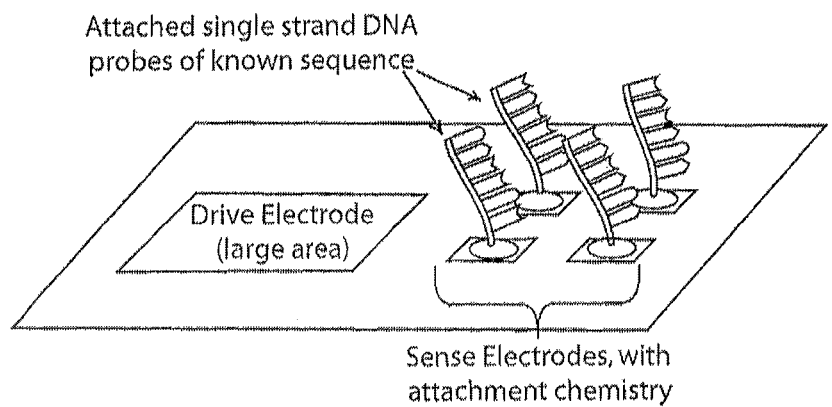
FIG. 2 is a schematic of exposed electrode array with attachment chemistry and affinity probes attached to the sense and reference electrodes.

FIG. 2 shows a representation of sense and reference electrodes coated with chemistries of attachment and attached DNA probes (scales are not relative, ~100,000 single strand DNA oligonucleotides fit in a 1 um2 area. Also, probe length may vary, with lengths between 24-mer and 60-mer preferred).

Figure 3:
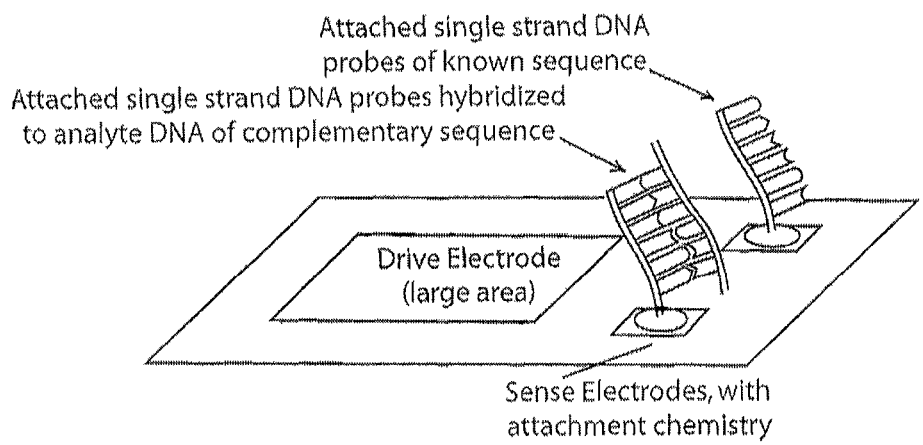
FIG. 3 is a schematic showing analyte (e.g. complementary sequence DNA) bound to affinity probe on a sense electrode.

FIG. 3 shows a representation of attached single strand DNA probe unhybridized and a double strand DNA representing a probe that has found a complementary match from the sample solution and hybridized.

A device including one or more integrating charge amplifiers is preferably configured to measure the integrated charge and effective capacitance at the analyte-electrode interface. A change in integrated charge or effective capacitance can then be used to ascertain whether the analytes have bound at the electrode surface or to the affinity probe attached to the electrode surface. This configuration need not be specific to any analyte but preferably can be applied to all analytes.

When measuring the effective capacitance, preferably the analyte is provided in a conductive solution that provides a conductive path between the driving and integrating electrodes of the amplifier, for example a conductive solution, such as liquid aqueous solution, or a conductive gel. A preferred method of using the device including one or more integrating charge amplifiers includes providing a voltage pulse through the drive electrode to the conductive matrix including the analyte. This pulse can be applied to the matrix with respect to an integrating electrode and the charge can be accumulated on the integrating electrode over a fixed time.

The measured capacitance is established by the fixed sensing electrode, the dielectric formed by the attachment chemistry, attached probe, and bound analyte (if a match is found), and a virtual parallel plate formed above the sense electrodes by the charge/ion distribution in the matrix. The measured capacitance is a function of the electrode area, the dielectric constant, and the distance of the virtual plate from the sensing electrode. Analytes binding to the electrode or attached affinity probe will change the dielectric constant and/or distance between the virtual plate and sense electrode, thereby changing the effective capacitance and accumulated charge on the sense electrode when a voltage is applied. The area and distance to the drive electrode are not material since the conductive matrix carries the voltage to the virtual plate. Any capacitance contributed by the drive electrode is in series with the measured capacitance and is small owing to the large electrode area.

To compensate for any noise at the time of the test (due to 1/f noise, thermal noise, etc.) a calibrating reference pulse is preferably applied to an internal test capacitor to normalize the response of the amplifier during each measurement cycle (this is different from the reference electrode). The output of this amplifier can then be digitized and post-processed. Post-processing is an algorithm that is applied through software to remove random noise, slopes, etc. The parameters can be determined experimentally by characterizing the various contributing parameters: e.g., electrode size, drive voltage, environmental conditions such as temperature, analyte binding concentration, etc.

Preferably, individually addressable sensing electrode arrays of various effective areas are created to increase the detection range of the amplifier to various concentrations of target in the solution. A large array of driving electrodes can be created to allow close coupling of driving voltage to the solution. Since the drive electrode capacitance is in series with the sense electrode interface+probe/target through the solution, preferably the driving electrode area is larger than sensing electrode area to reduce parasitic effects. A system comprised of a large capacitor in series with a small capacitor is dominated by the small capacitor. In this case: $1/C\ series = 1/Cintegrated + 1/Cdrive \rightarrow 1/Cintegrated$ as Cdrive gets large.

An array of integrating amplifiers and respective electrode arrays are preferably fabricated on the same substrate, (also synthesis and detection drive circuits, may also include logic for switching, latches, memory, IO devices, and other device able to be integrated in silicon)

For improved sensitivity, preferably a device that includes one or more reference electrodes is used for differential measurements. Reference and sensing electrode routing paths can be matched in a layout pattern to reduce parasitic coupling.

Figure 4:
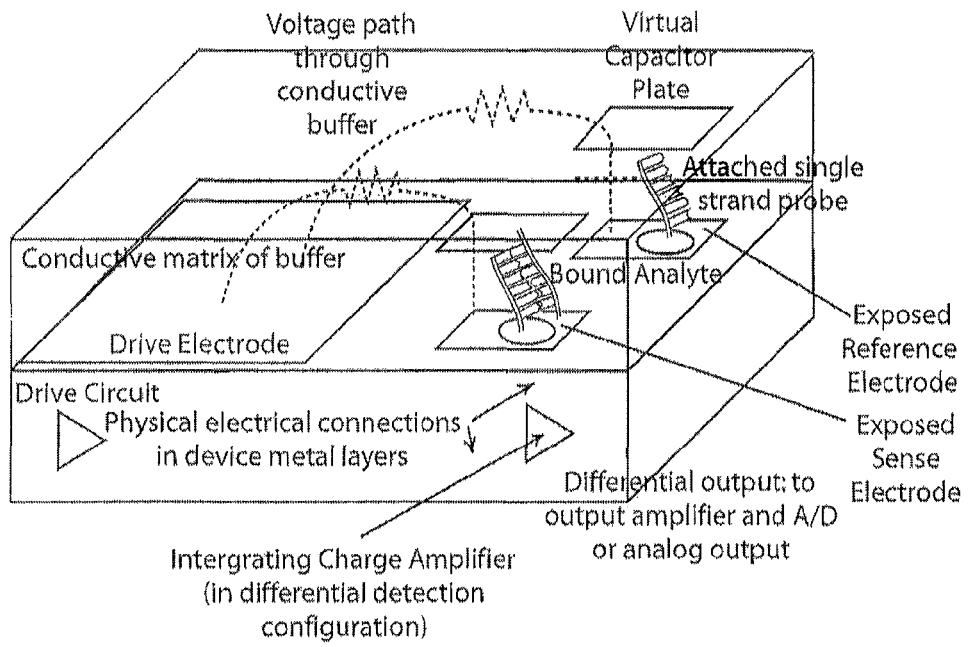
FIG. 4 is a schematic of a device operating in differential detection mode with key elements and electrical connections shown.

Preferably, the measurement of the change in capacitance at the sensing electrode is accomplished in one of two manners. First, the change can be detected with respect to the exposed reference capacitor. In this embodiment, the reference electrode is exposed to the same solution as the sensing electrode. Preferably, a probe that is designed to have similar electrical characteristics as the affinity probed but not to bind to a target in the solution in attached to the reference electrode. A change in integrated charge is measured as binding occurs on the sensing electrode (or affinity probe attached thereon) whose electrical characteristics change, but not on the reference electrode whose electrical characteristic remain the same. Second, two measurements of the same electrode, before and after the analyte binds, can be compared to establish the change in integrated charge resulting from binding. In this case, the same electrode at a previous time provides the reference. FIG. 4 shows an example of a device configured to operate in this fashion. In FIG. 4 the dotted lines show resistance and capacitive paths established by the conductive matrix and insulating affinity probe/analyte layer on the electrode. This schematic shows the device operation in differential detection mode, in which both reference and sense electrode have attached affinity probes (of different affinity) to reject common mode noise contributed by the matrix and other parasitics and noise sources.

Figure 5:
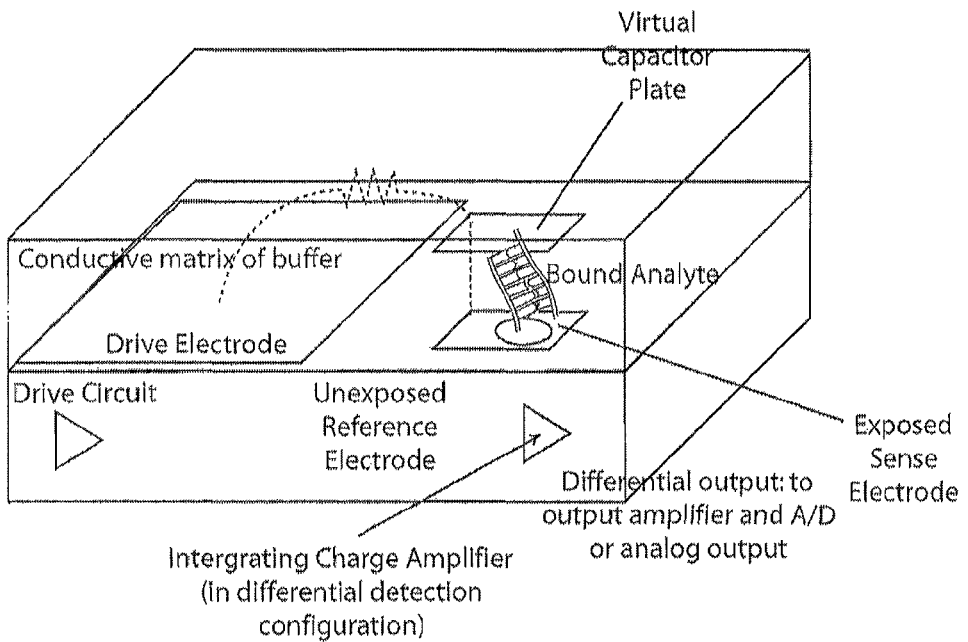
FIG. 5 is a schematic of device operating in absolute detection mode with key elements and electrical connections shown.

In an alternative configuration, the reference electrode can be configured so that the sensing electrode takes direct capacitance measurements (non-differential). In this configuration, the reference electrode can be covered with a small dielectric substance such as epoxy or the device passivation or left exposed to air. The signal from the electrode can then be compared to an open circuit which establishes an absolute reference for measurement but may be more susceptible to noise. FIG. 5 shows an example of a device in an absolute detection mode, in which the reference is an unexposed (or exposed to a fix environment such as air) fixed capacitor.

This device preferably provides real-time detection capability. In more traditional approaches, all of the sample analytes are tagged with an optical label (Cy dye, FITC, etc.). To determine what has bound to the surface, the sample must be washed off after a time to remove unbound analytes and their associated labels. This wash stops all kinetics of the analytes and electrode/probes. In this invention, analytes are not tagged and detection is electrical, so washing is not needed to remove unwanted signal. Therefore real-time monitoring of binding kinetics can be accomplished by providing dynamic measurement at the solid-solution interface by applying a pulse and integrating the response at various times during the development of hybridization. In other words, since no wash is required to remove the unbound but labeled analytes, the invention can operate without the experiment being halted with the wash.

Preferably, the device has a digital mode capability. For example, a 1 bit latch can be provided on the chip device. The response of the amplifier to a drive or reference pulse can then be stored in this latch. For instance, the response can be above or below the response of the reference electrode. By varying the value of the drive or reference pulses and capturing the responses to these pulses more than 1 bit resolution can be obtained. Parallel operation of a large number of sensing nodes and amplifiers can be done this way. Alternatively, an analog signal can be read out directly or digitized through an internal or external analog to digital converter.

Figure 6:
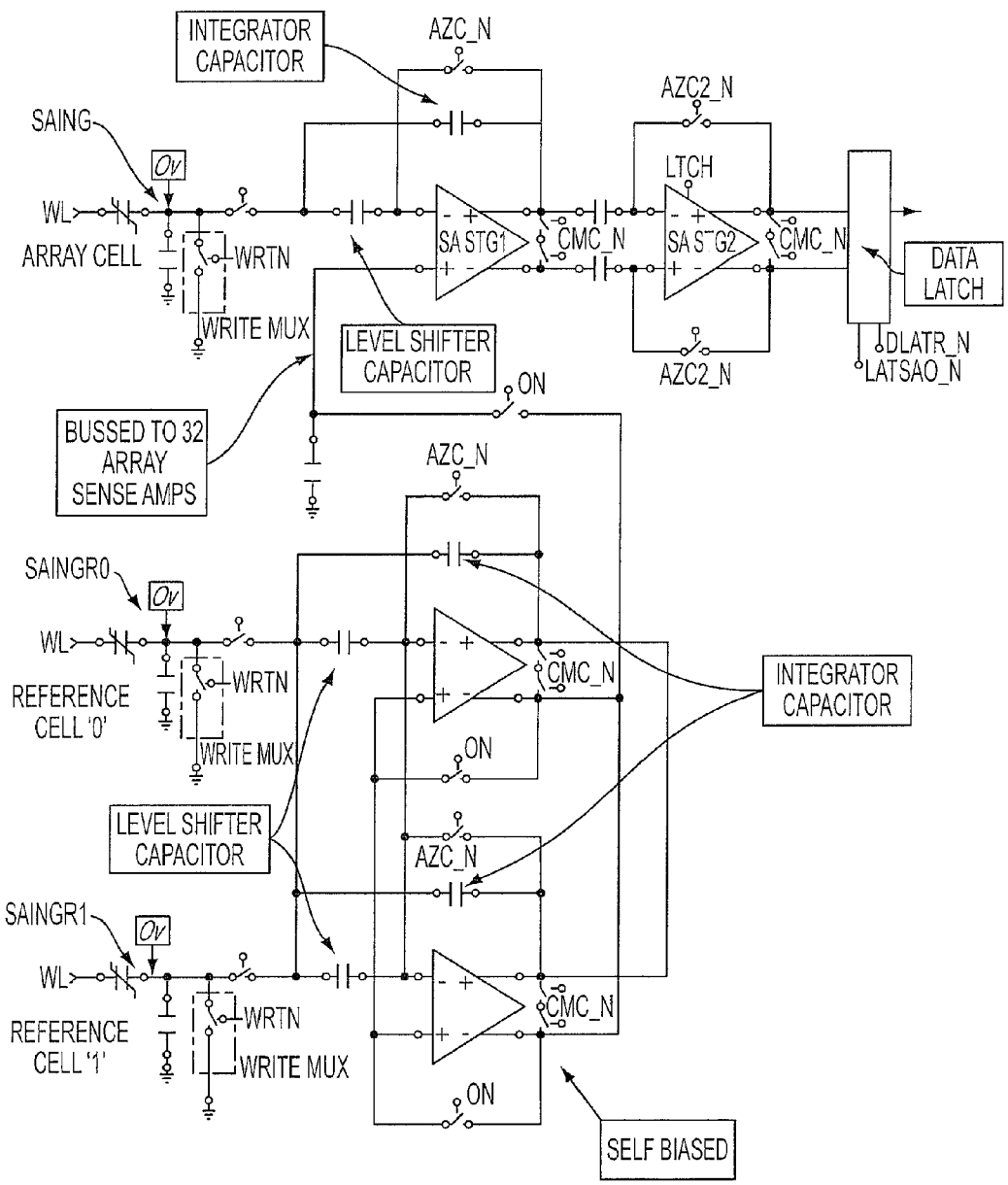
FIG. 6 is a circuit schematic of a detection device showing connection of the sense and reference electrode capacitors, internal switches, etc.

FIG. 6 is a circuit schematic of a detection device showing connection of the sense and reference electrode capacitors, internal switches, etc.

Figure 7:
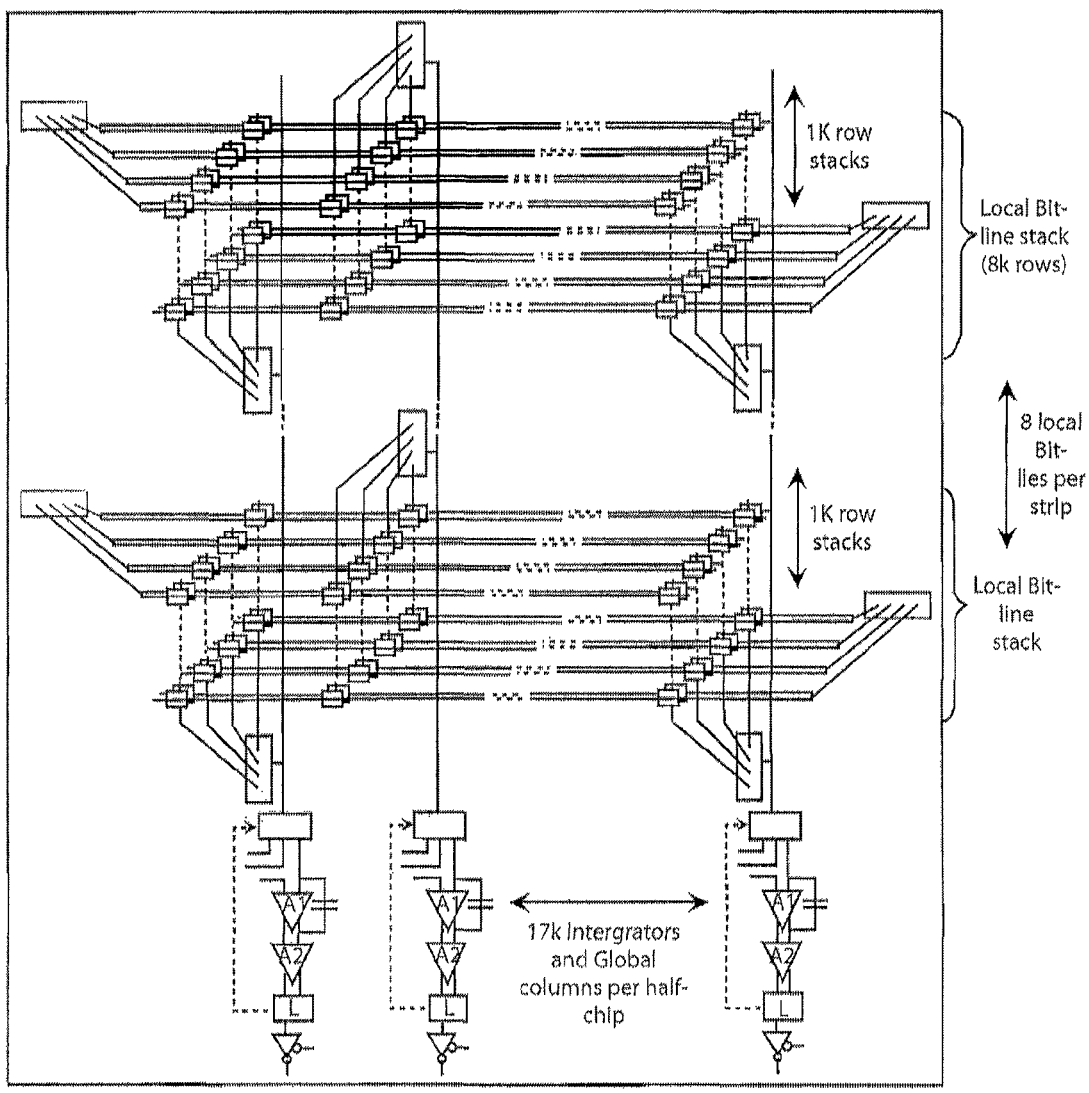
FIG. 7 is a circuit schematic of the device showing connection of the addressing circuits and attached amplifiers.

FIG. 7 is a circuit schematic of the device showing connection of the addressing circuits and attached amplifiers.

Figure 8:
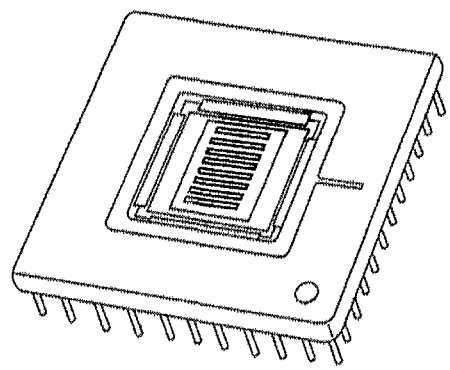
FIG. 8 is an image of a completed device prototype according to the invention.

FIG. 8 is an image of a completed device prototype according to the invention.

Figure 9:
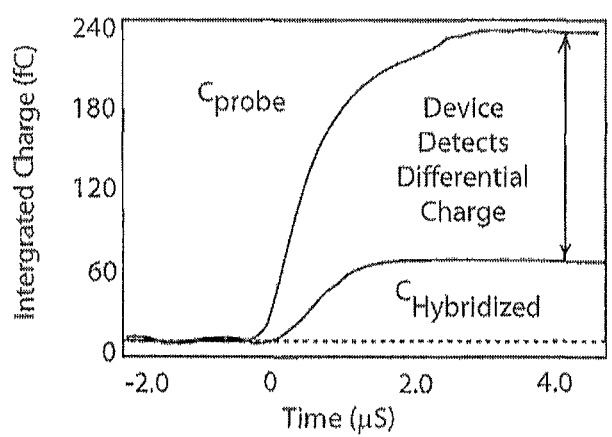
FIG. 9 is a graph showing how the device operates to detect analyte binding.

FIG. 9 is a graph showing how the device operates to detect anyltye binding. In FIG. 9 device measurement of integrated charge on two electrode: the first (red) with attached affinity probe only and the second (green) with analyte bound to attached affinity probe. In this experiment, the affinity probe and analyte are single strand oligonucleotides.

Another embodiment is a method and device for electrochemically synthesize polymers. The electrodes may be the same electrodes used to detect analyte bindings with circuitry to connect them to either drive circuitry or the integrating charge amplifiers.

Preferred polymers that are manufactured include, but are not limited to, DNA oligonucleotides, peptides, and aptamers.

The electrodes may be made from a variety of materials utilized in standard CMOS fabrication. Preferred electrode materials include Ti, TiN, and Ta. Alternatively, materials that are compatible with a CMOS fabrication process but not traditionally used, such as Au and Pt, can be employed in this invention.

During polymer synthesis, the electrodes are used to control the acidic or basic region directly above them. For example, micron and/or sub-micron exposed surface area, confinement electrodes of opposite polarity or floating separate attachment electrodes that may be grounded or floating. Having these drive voltage options allows the user to optimize the chemistry for the synthesis preferred. For example, the drive electrode can source the voltage that creates the acid field, the floating electrode can be placed so that the chemistry is optimal for synthesis, and the electrode of opposite polarity can quench the acid or base to confine the reaction to the desired area. One skilled in the art will understand how to appropriately drive these electrodes to maximize the electrochemical synthesis process. Preferably, the electrode on which the polymer is synthesized is also the electrode connected via circuitry to the integrating charge amplifier.

Preferably, large arrays of electrodes are arranged on a substrate. The electrodes are preferably, in various arrangements and sizes on the same substrate to enable a diversity of polymers and multiplexing of individual electrodes to create polymers of desired sizes and shapes.

Preferably, one or more distinct voltage pulses can be applied to the each of the electrodes. This allows creation of an active or group of active electrodes surrounded by an array of confinement electrodes without addition of any other special function electrodes. In other words, multiple electrodes can be similarly driven to create larger regions of acid or base field. Likewise, multiple electrodes can be used to form a common attachment or quenching region.

Figure 10:
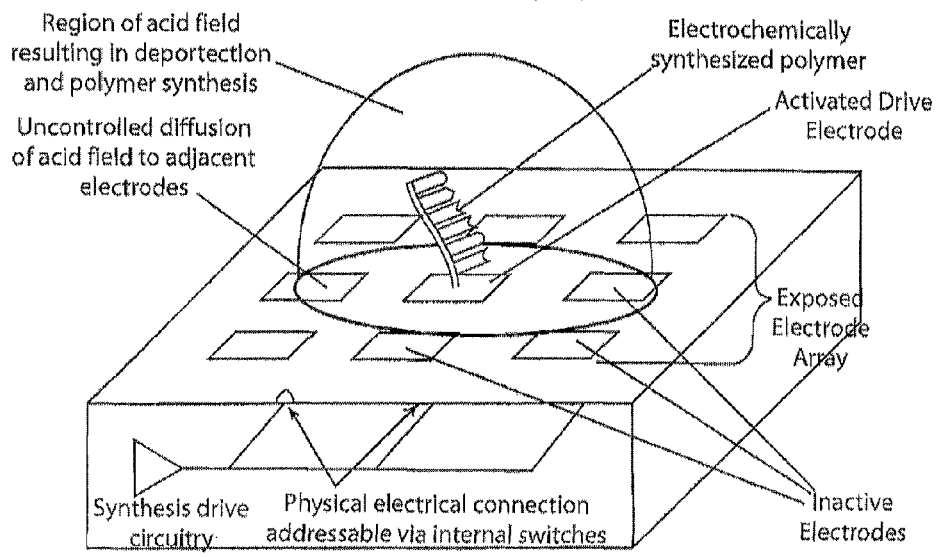
FIG. 10 is a schematic of a device in electrochemical synthesis of polymer affinity probe operation.

FIG. 10 is an example of a device in electrochemical synthesis of polymer affinity probe operation. The acid/base field generated by the activated electrode deprotects an existing attachment chemistry or polymer base allowing subsequent base attachment. Note the acid/base field is free to diffuse across the surface of the device when other electrodes are inactive. Also note that the exposed electrodes can be the same as those used in the detection operation.

Figure 11:
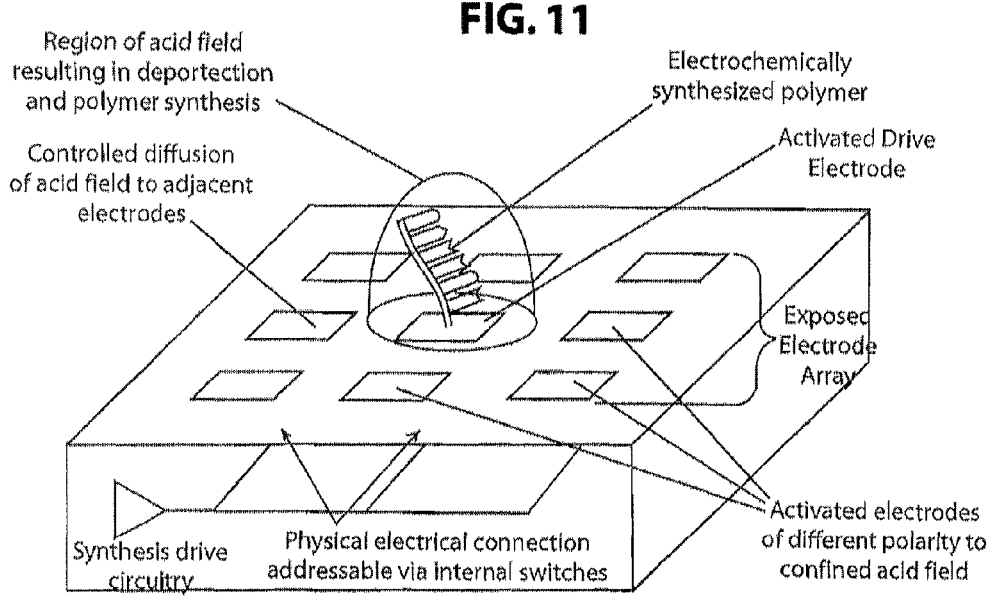
FIG. 11 is an alternative configuration of a device in electrochemical synthesis of polymer affinity probe operation.

FIG. 11 is an alternative configuration of a device in electrochemical synthesis of polymer affinity probe operation. The acid field generated by the activated electrode deprotects an existing attachment chemistry or polymer base allowing subsequent base attachment. Note the acid field confined in this mode of operation when surrounding electrodes are activated to the opposite polarity (or otherwise driven appropriately to quench the acid or base field), Again note that the exposed electrodes can be the same as those used in the detection operation.

Figure 12:
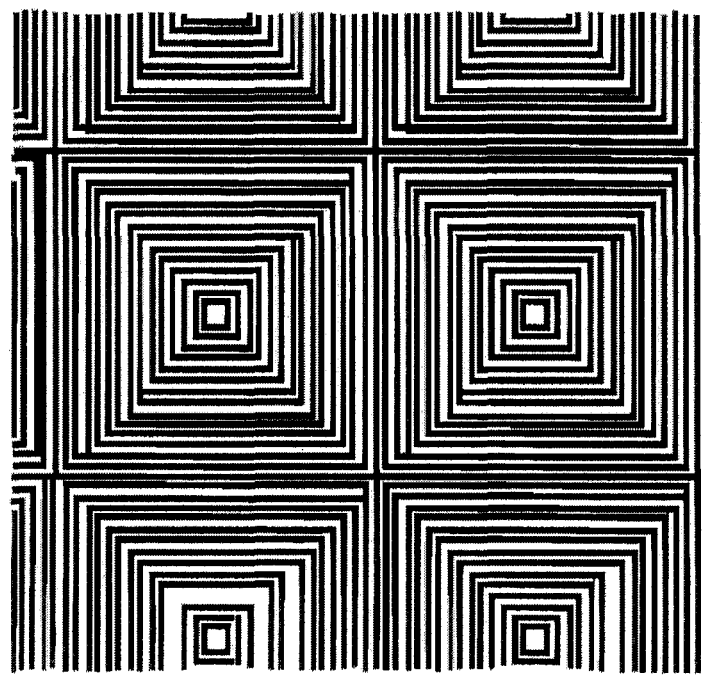
FIG. 12 is an image of an electrode pattern in which concentric rings are used to more effectively confine the acid/base field.

In another embodiment, electrode can be used that have arbitrary size and shape to define the chemistry. For example, a confinement electrode can be a ring of metal around the drive and/or floating electrode. FIG. 12 is an image of a synthesis electrode pattern in which concentric rings are used to more effectively confine the acid/base field. Again note that the exposed electrodes can be the same as those used in the detection operation. The electrode size and shape are immaterial.

Preferably, a set of two latches are provided at each active electrode site to allow the electrode to exist in three states driven by voltage 1, driven by voltage 2, or floated during the synthesis cycle.

The voltage sources for the electrodes on the device can be internally multiplexed from external sources through digital control, and preferably can be applied in parallel to a large array of electrodes.

In application, voltages are applied to a programmed selection of electrodes as a solution of polymer base is flowed over the electrodes. The applied voltage creates an acidic or basic field that deprotects the polymer base so that it attaches to the electrode surface, surface chemistry, or previous base. By flowing different bases over the electrodes with the desired programmed electrode activation, the polymer sequence is generated at each electrode.

Yet another configuration is a method and device to synthesize polymers and detect binding to the polymer on a common integrated device surface. The device may be the same device used to detect analyte bindings and synthesize polymers previously described. The device is capable of carrying out on-chip electrochemical polymerization reactions (functionalization) and also on-chip label-free analyte detection.

Polymers that can be synthesized and detected utilizing the devices and methods include, but are not limited to, DNA oligonucleotides, peptides, and aptamers. Bindings include, but are not limited to, DNA hybridization, peptide/protein binding, peptide phosphorylation, and aptamer/protein binding. Detection devices include those that can be integrated with the synthesis devices, for example field effect devices (direct and floating gate), impedance spectroscopy devices, integrating charge amplifiers, and optical devices capable of being integrated with electro-chemical synthesis devices. Preferred devices include devices that utilize integrated charge amplifiers.

In one preferred configuration, the same CMOS circuitry that enables the voltage outputs of the electrochemical synthesis reactions above are designed to be easily re-programmed for electrical detection. In particular, the sensing AND synthesis electrodes can be individually addressed, and any electrode can behave as detection, driving, active synthesis or shielding electrode.

Preferably, the device includes one or more integrating charge amplifiers and one or more electrodes capable of being driven to a given voltage in a pulsed manner, or in any arbitrary shape. Preferably, large arrays of electrodes of various sizes are arranged on the same substrate.

Preferably, one or more voltage patterns can be applied to the each of the electrodes. This allows creation of an active or group of active electrodes surrounded by an array of shielding electrodes without addition of any other special function electrodes Preferably, a set of two latches are provided at each site to allow the electrode to exist in the three states: driven by voltage 1, driven by voltage 2, or floated during the synthesis cycle.

Preferably, the voltage sources are internally multiplexed from external sources through digital control, and can be applied in parallel to a large array of electrodes. By modulating voltages at electrodes on a case-by-case basis, synthesis chemistries can by tailored to the particular requirements of each electrode.

The same CMOS circuitry and electrodes used for voltage outputs of the electrochemical synthesis reactions can also be used to detect bindings. Integrating charge amplifiers are preferably utilized to measure the changes in charge and effective capacitance at the analyte-electrode interface.

Preferably, a pulse of voltage is applied to the solution with respect to an integrating electrode and the charge is accumulated over a fixed time. A calibrating reference pulse can be applied to the solution through an internal test capacitor to normalize the response of the amplifier during each measurement cycle.

Preferably, a two stage integrating charge amplifier to convert the charge to a voltage.

Logic circuits can be used to digitize and post-process the output of the two stage integrating amplifier. Post-processing removes random noise, slopes, etc. These circuits can be on the same chip or off chip.

Individually addressable sensing electrode arrays of various effective areas can be used to increase detection range. Preferably, a large array of driving electrodes is created to allow close coupling of driving voltage to the solution. In addition, preferably the driving electrode area is larger than sensing electrode area to reduce parasitic effects.

In application, voltages are applied to a programmed selection of electrodes as a solution of polymer base is flowed over the electrodes. The applied voltage creates an acidic or basic field that deprotects the polymer base so that it attaches to the electrode surface, surface chemistry, or previous base. By flowing different bases over the electrodes with the desired programmed electrode activation, the polymer sequence is generated at each electrode.

A sample solution can be applied to the electrode array with polymers sequences attached. Where the analytes in the sample have affinity with the attached polymer, they bind.

The detection circuits can used with the same electrodes as described above to detect the change in capacitance of the electrode interface. In this manner, an integrated synthesis/detection device can use a common set of electrodes to synthesize polymers and detect binding. This method offers unprecedented capabilities for merging highly flexible polymer Real time Polymerase Chain Reaction (PCR) Monitoring Progress of DNA amplification during a Polymerase Chain Reaction (PCR) can be monitored in "real time" by measuring capacitance change at each feature location. Reaction rates can be measured continuously, or determined at a fixed time point during the exponential amplification phase. A computer can be used to measure the rate of capacitance change of all simultaneous experimental PCR reactions occurring on the detection chip. Unlike ordinary preparative PCR, RT-PCR allows the success of multiple PCR reaction to be determined automatically after only a few cycles, without separate analysis of each reaction, and avoids the problem of "false negatives".

PCR Assay Protocol

Typical PCR protocols can be followed. The number of copies of total RNA used in the reaction are preferably enough to give a signal by 25-30 cycles. The optimal concentrations of the reagents are as follows: i. Magnesium chloride concentration should be between 4 and 7 mM. ii. Concentrations of dNTPs should be balanced with the exception of dUTP (if used), iv. The optimal probe concentration is 50-200 nM, and the primer concentration is 100-900 nM. AmpErase uracil-N-glycosylase (UNG) is added in the reaction to prevent the re-amplification of carry-over PCR products by removing any uracil incorporated into amplicons. It is necessary to include at least three No Amplification Controls (NAC, a minus-reverse transcriptase control) as well as three No Template Controls (NTC, a minus sample control) in each reaction plate (to achieve a 99.7% confidence level in the definition of +/−thresholds for the target amplification, six replicates of NTCs must be run). NAC is a mock reverse transcription containing all the RT-PCR reagents, except the reverse transcriptase; NTC includes all of the RT-PCR reagents except the RNA template.

Electrochemical Biochip Design

To configure the chip for RT-PCR a set probes, oligonucleotides or cDNA fragments, are selected and optimized from target sequences based on the criteria of specificity of the hybridization with the target sequence, uniform inching temperature of the probes, and secondary structure stability. The following strategies for efficient selection of probe sequences satisfying these criteria are considered: 1) Removal of exactly repetitive sequences: to efficiently find sequences appearing in more than one open reading frame (ORF), and remove them from candidates for probe sequences. 2) Minimization of frequency of occurrence: to estimate the frequency of occurrence of a probe sequence based on the frequency of occurrence of all k-tuples consisting of a probe sequence. Only rarely occurring sequences are selected for probe candidates. 3) Unifying melting temperature: to calculate the melting temperature of matching probe. The filter classifies probe sequences into fewest groups with a uniform melting temperature. All DNA probes on a chip surface are subjected to the same hybridization and wash conditions. Therefore, the uniform melting temperature minimizes false-positive and/or false-negative signals, making accurate target identification possible. 4) Filtering secondary structure stability: to calculate the free energy of optimal secondary structure of probe. Stable intra-strand secondary structure of probe hinders rapid hybridization to a target sequence, resulting in extensive decrease of the signal intensity. This filter removes those unfavorable probe sequences. 5) Minimization of Hamming distance: to calculate the minimum Hamming distance between a probe sequence and a target sequence. It examines the specificity of probe.

On-Chip PCR

Figure 13:
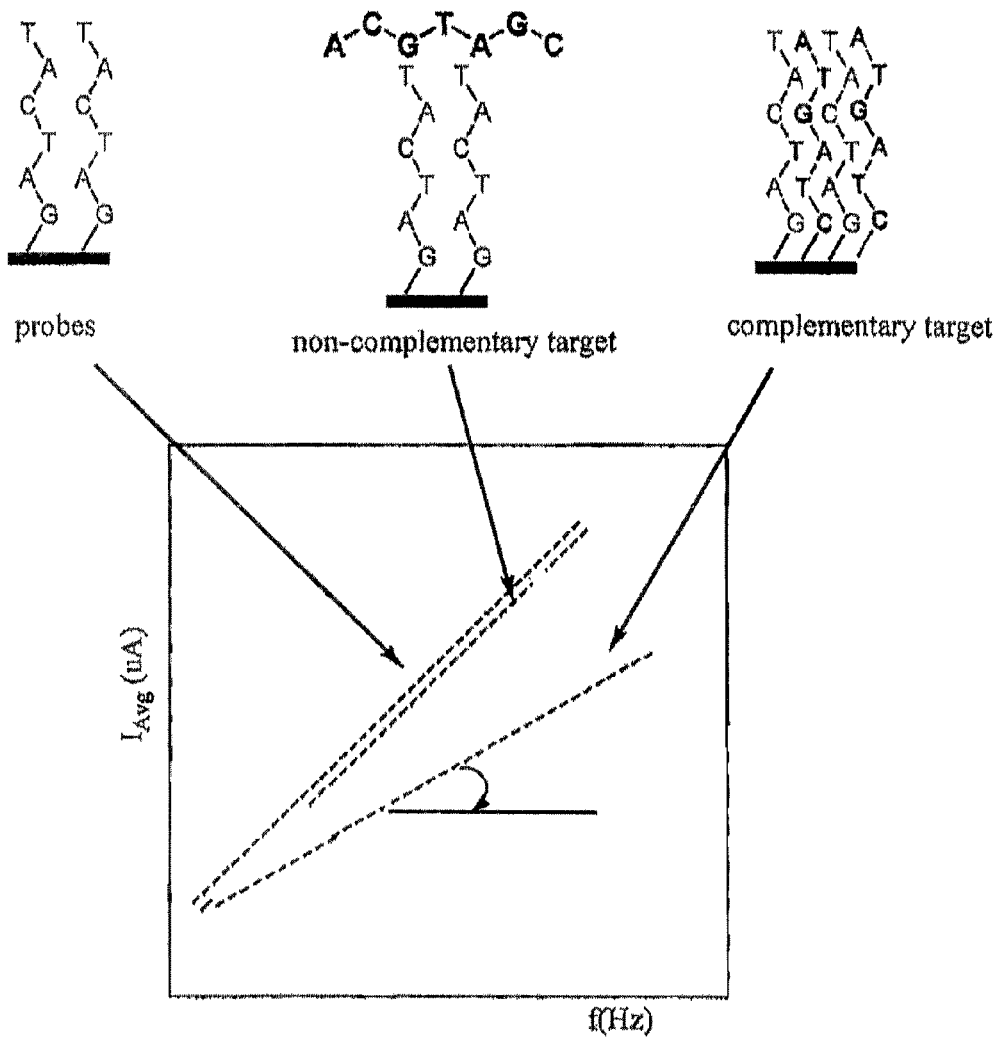
FIG. 13 is a graph of capacitance change as a function of the number of replicated targets.

As shown in FIG. 13, in contrast to conventional PCR, the reaction is performed directly on chip and reaction products are measured by capacitance change. The underlying principle of sequence detection is based on the well-known process of semi-nested PCR. On-chip PCR includes liquid phase PCR with two sequence-specific primers, which is performed on the chip with covalently bound nested, allele-specific PCR primers. PCR products generated in the liquid phase are then re-amplified in a semi-nested PCR directly on the chip surface. Thus in on-chip PCR amplification and sequence detection are combined within a single step. The oligonucleotide microarray is designed such that positive signals reveal the presence and nature of the target DNA of interest. On-chip PCR can be employed to identify single nucleotide polymorphisms (SNPs) in human genomic DNA. On-chip PCR can be used for detection and identification of pathogens. This has the benefits of combining conventional PCR amplification with microarray technology for the development of simple and rapid DNA diagnostic systems.

This application discloses several numerical range limitations that support any range within the disclosed numerical ranges even though a precise range limitation is not stated verbatim in the specification because the embodiments of the invention could be practiced throughout the disclosed numerical ranges. Finally, the entire disclosure of the patents and publications referred in this application, if any, are hereby incorporated herein in entirety by reference.

The invention claimed is:

1. A method for synthesizing a polymer on a surface of at least one sensing electrode of a device, the method comprising:
exposing the at least one sensing electrode to one or more monomer bases; and
binding the one or more monomer bases on the surface by creating an acidic or basic field that deprotects the one or more monomer bases, wherein the device comprises:
at least one drive electrode, the at least one sensing electrode and at least one reference electrode on a surface of a substrate; and
an integrating charge amplifier connected to the at least one sensing electrode and configured to detect the change in charge or effective capacitance on the surface of the at least one sensing electrode due to binding of the one or more monomer bases to the at least one sensing electrode,
wherein the at least one sensing electrode comprises a sensing routing path, the reference electrode comprises a reference routing path and the sensing routing path and reference routing path are matched and wherein the reference electrode configured to provide differential measurements of change in charge and effective capacitance;
wherein the device further comprises a confinement electrode and wherein the acidic or basic field is confined in a vicinity of the surface by the confinement electrode.

2. The method of claim 1, wherein the polymer is a DNA oligonucleotide, a peptide, or an aptamer.

3. The method of claim 1, wherein the acidic or basic field is created by applying a voltage to the at least one sensing electrode.

4. The method of claim 1, wherein the one or more monomer bases are in an aqueous solution or conductive gel.

5. The method of claim 1 wherein the acidic or basic field is created by applying a voltage to the at least one drive electrode and electrically floating the at least one sensing electrode.

6. The method of claim 1, further comprising applying one or more voltage pulses to the at least one drive electrode the at least one sensing electrode.

7. The method of claim 1, wherein the acidic or basic field is free to diffuse.

8. The method of claim 1, wherein the confinement electrode is a ring around the at least one drive electrode or the at least one sensing electrode.

9. The method of claim 1, wherein the one or more monomer bases comprise different bases.

10. The method of claim 1, wherein the one or more monomer bases are bound to the surface directly, or indirectly through an existing base on the surface or through a surface chemistry on the surface.

11. The method of claim 1, further comprising flowing the one or more monomer bases over the surface.

12. The method of claim 1, wherein the at least one sensing electrode is part of an array of electrodes fabricated on a single substrate.

13. The method of claim 1, wherein the device further comprises a one-bit latch.

* * * * *